United States Patent [19]
Hinshaw

[11] Patent Number: 5,711,786
[45] Date of Patent: Jan. 27, 1998

[54] GAS CHROMATOGRAPHIC SYSTEM WITH CONTROLLED SAMPLE TRANSFER

[75] Inventor: John V. Hinshaw, New Fairfield, Conn.

[73] Assignee: The Perkin-Elmer Corporation, Norwalk, Conn.

[21] Appl. No.: 734,689

[22] Filed: Oct. 21, 1996

Related U.S. Application Data

[60] Provisional application No. 60/006,017, Oct. 23, 1995.

[51] Int. Cl.[6] ............................................. B01D 15/08
[52] U.S. Cl. .................... 95/82; 73/23.25; 73/23.42; 96/102; 96/103; 96/105
[58] Field of Search ..................... 73/23.35, 23.36, 73/23.42; 95/82, 89; 96/101–103, 105

[56] References Cited

U.S. PATENT DOCUMENTS

| | | | |
|---|---|---|---|
| 3,208,230 | 9/1965 | Fourroux | 96/102 X |
| 3,751,966 | 8/1973 | Ryan et al. | 96/103 X |
| 3,881,892 | 5/1975 | Gehrke et al. | 96/103 X |
| 4,180,389 | 12/1979 | Paul | 96/101 X |
| 4,237,733 | 12/1980 | Kolb et al. | 73/423 |
| 4,464,940 | 8/1984 | Pospisil | 73/864.21 |
| 4,476,733 | 10/1984 | Chlosta et al. | 73/863.91 |
| 4,484,483 | 11/1984 | Riegger et al. | 73/864.23 |
| 4,554,436 | 11/1985 | Chlosta et al. | 219/385 |
| 4,773,552 | 9/1988 | Boege et al. | 215/247 |
| 4,994,096 | 2/1991 | Klein et al. | 55/20 |
| 5,108,466 | 4/1992 | Klein et al. | 95/82 X |
| 5,163,979 | 11/1992 | Patrick et al. | 95/82 X |
| 5,339,673 | 8/1994 | Nakagawa et al. | 73/23.36 |
| 5,391,221 | 2/1995 | Fukushima et al. | 95/82 |
| 5,403,386 | 4/1995 | Collier et al. | 96/105 |
| 5,431,712 | 7/1995 | Henderson et al. | 95/82 X |
| 5,467,635 | 11/1995 | Nakagawa et al. | 73/23.42 X |
| 5,545,252 | 8/1996 | Hinshaw et al. | 95/82 X |
| 5,547,497 | 8/1996 | Klemp et al. | 96/105 X |
| 5,567,227 | 10/1996 | Henserson | 95/82 X |

OTHER PUBLICATIONS

John V. Hinshaw, "The Effects of Inlet Liner Configuration and Septum Purge Flow Rate on Discrimination in Splitless Injection", vol. 16, Apr. 1993, Journal of High Resolution Chromatography, pp. 247–253.

*Primary Examiner*—Robert Spitzer
*Attorney, Agent, or Firm*—David Aker; Herbert S. Ingham

[57] ABSTRACT

In a gas chromatographic system that includes a column and an injector with a chamber, a carrier gas normally flows into the chamber at a constant rate, and a constant primary pressure is maintained at the column inlet. A sampling receptacle selectively communicates a sample vessel with a source of transfer gas or the chamber. The vessel is pressurized with the transfer gas to a starting pressure greater than the primary pressure. Analyte sample in transfer gas is then tranferred from the vessel to the chamber by the vessel pressure while the vessel pressure remains greater than the primary pressure. Carrier gas flow is discontinued during transfer, so that analyte sample transfers through the chamber into the column by the primary pressure linearly with time. Standby and venting states are provided.

16 Claims, 4 Drawing Sheets

GAS CHROMATOGRAPHIC SYSTEM WITH CONTROLLED SAMPLE TRANSFER

This application claims the benefit of U.S. Provisional Application Ser. No. 60/006,017 filed on Oct. 23, 1995.

This invention relates generally to gas chromatographic systems and particularly to control of sample transfer into such a system.

BACKGROUND

Gas chromatography is essentially a physical method of separation in which constituents of a test sample in a carrier gas are adsorbed and desorbed by a stationary phase material in a column. A pulse of the sample is injected into a steady flow of carrier gas. At the end of the column the individual components are more or less separated in time. Detection of the gas provides a time-scaled pattern which, by calibration or comparison with known samples, indicates the constituents of the test sample. The main components of such a system are the column, an injector for introducing the sample into carrier gas and passing the mixture into the column, a means for transferring sample into the injector, a detector at the outer end of the column, gas controls, and a device such as a computer for treating and displaying the output of the detector. An oven may be used to elevate temperature to maintain the sample in a volatile state, and to improve the discrimination of constituents.

In the use of open tube or packed capillary types of columns, only a small flow of carrier gas with the sample is desired, whereas it is more accurate and convenient to inject larger quantities of the sample. Therefore, a small portion of the gas mixture is bled into the column and the major portion is split off and vented. Such a system is known as a "split injection" system. The injector generally contains a septum through which sample is injected. The septum may have a fixed tube inserted therein which connects back to a sampler with a needle that is inserted into a diaphragm on a pressurized sample vial. A mixing chamber in the injector usually has an outlet for a purge gas that is a portion of the carrier gas passed along the septum. The purge gas removes vapors emitted from the septum during operation at elevated temperature, as the vapors otherwise could contaminate the carrier and its test sample flowing to the column.

Several alternative means are used for control of carrier gas flow in the injector. One is back-pressure regulated from an outlet line, with mass flow being controlled in the inlet line to the injector. The septum purge is effected through a restriction in the outlet line to maintain small purge flow and a selected pressure in the injector. In newer systems electronic pressure sensors control variable restrictors to regulate flow and pressure.

One means of injection of a sample (containing analyte) from a sample vial is known as "headspace sampling". In conventional headspace sampling, sample material (solid, liquid, gas or a mixture thereof) is sealed in a vial and subjected to constant temperature conditions for a specified time. Analyte concentrations in the vial gas phase should reach equilibrium with the liquid and/or solid phases during this thermostatting time. The vial is subsequently pressurized with carrier gas to a level greater than the "natural" internal pressure resulting from thermostatting and equilibration. Then the pressurized vial is connected to the GC column with a hypodermic type of needle which is inserted into the vial for a short period of time to transfer a portion of the vial gas phase into the column. This type of headspace sample transfer from the sample vial is commonly known as "balanced-pressure sampling". The vial pressure may be relieved after sample transfer, for subsequent repetitive sampling from the same vial, in a multiple headspace extraction (MHE) technique.

In the conventional system of sampling, the total amount of sample transferred into the column depends, among several parameters, on the sample transfer time period. The amount of sample injected is not a linear function of the time, but depends on the rate of pressure decay in the vial during the sampling period. At low sample flow rates from the vial, the pressure decays slowly, and the sample amount is approximately linear with time. At high flow rates the pressure decays rapidly, and the sample amount is determined by exponential pressure decay which generally is not readily or accurately ascertained.

A second problem with present systems is that the headspace vial pressure is controlled relative to ambient (atmospheric) pressure. Significant ambient pressure fluctuations will affect the amount of sample transferred into the column in such systems, since the column flow rate during sample transfer is a function of the ambient pressure.

Another problem is that, in MHE sampling, the vial pressure is vented to ambient pressure between analyses. The venting procedure extracts a portion of sample from the headspace vial, and the amount of sample extracted should be held constant. If the ambient pressure varies, the extracted sample also varies.

An object of the invention is to provide an improved gas chromatographic system having a reproducible and readily determinable amount of sample transfer. A more particular object is to provide a gas chromatographic system in which transfer of sample into the gas chromatographic column is linear with time. Another object is to provide such a system in which the sample transfer is independent of ambient pressure.

SUMMARY OF THE INVENTION

The foregoing and other objects are achieved, at least in part, with a gas chromatographic system having a gas chromatographic column with a column inlet, and an injector means with a chamber selectively receptive of a carrier gas flow and an analyte sample in a transfer gas. The chamber communicates with the column inlet for injecting gas and sample into the column. A flow means effects the carrier gas flow into the mixing chamber at a constant flow rate, and includes a means for discontinuing the carrier gas flow during a transfer period. A primary pressure means maintains a constant primary pressure at the column inlet. The system includes a transfer pressure source of a transfer gas, and a transfer means for selectively communicating a sample vessel with the transfer pressure source or the mixing chamber. The sample vessel contains an analyte sample.

A control means is operatively connected with the transfer means for operating the chromatographic system through a set of operational states including, in sequence, a pressurizing state and a sample transfer state. In the pressurizing state, the sample vessel is pressurized with the transfer gas, with the sample vessel being in communication with the transfer pressure source so as to effect a vessel pressure at a starting pressure greater than the primary pressure. In the sample transfer state, analyte sample is transferred in the transfer gas from the sample vessel to the mixing chamber by the vessel pressure during a transfer period. This period is preselected so that the vessel pressure, while declining from the starting pressure, remains greater than the primary pressure. During the transfer period, the pressurizing and the carrier gas flow are discontinued. Analyte sample is thereby transferred through the chamber into the column by the primary pressure linearly with time during the transfer period.

Preferably the transfer means includes means for selectively communicating the sample vessel to ambient atmosphere, and the set of operational states further comprises a venting state for venting the sample vessel to ambient atmosphere. The venting state commences upon termination of the transfer period, with the sample vessel being in communication to ambient atmosphere, communication between the sample vessel and the mixing chamber discontinued, and carrier gas flow effected.

More preferably, the transfer means further includes a bleed line openable to atmosphere, with the transfer means being selectively receptive of a flush gas selected from transfer gas or carrier gas backflow from the chamber. The set of operational states further comprises a standby state prior to the pressurizing state, with the bleed line open and the transfer means receptive of the flush gas during the standby state.

Objects of the invention are also achieved by a method of effecting the foregoing states of operation.

DETAILED DESCRIPTION

Figure 1:
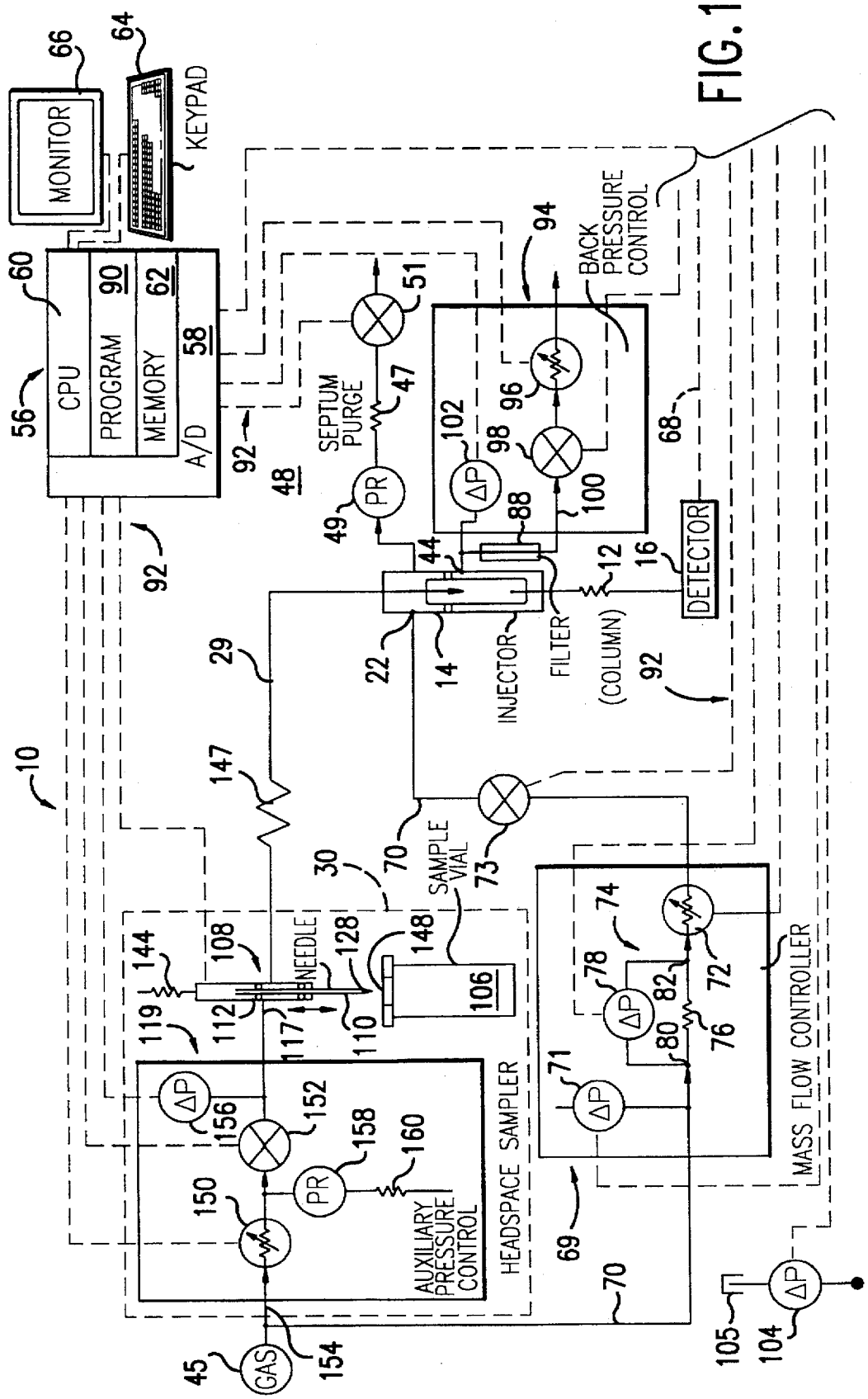
FIG. 1 is a schematic drawing of a gas chromatographic system according to the invention.

In a gas chromatographic system 10 illustrated in FIG. 1, a chromatographic column 12 is connected between an injector 14 and a detector 16. The system is a back-pressure type, as explained below. The column, injector and detector are conventional, such as those associated with a Perkin-Elmer AutoSystem GC equipped with an autosampler for sampling selected sources of test material. A type of column that particularly utilizes split flow is a capillary column. For example, the column may be formed of a 25 m long fused silica tube with 0.32 mm internal diameter and a 5 mm film of polydimethylsiloxane stationary phase. The column alternatively may be a packed open tubular column. The detector may be, for example, a hot wire, a flame ionization or a mass-spectrometric type; however, the actual detector is not critical to the present invention.

The injector means 14 (FIG. 2), which is conventional, is constructed typically of a tubular housing 18 with a mixing chamber 20 near the top (as shown, orientation not being important). The mixing chamber is receptive of a carrier gas through an inlet passage 22. At an injection fitting 24 above the chamber is a septum 26 which is a thick (about 0.5 cm) silicone rubber disk. Test sample material, generally a gas in headspace sampling is selectively injected from a transfer line 29 with a hollow needle 28 through the septum from a sampler 30 into the carrier gas to form a mixture. Sample material generally is injected only momentarily, so that the mixture is a pulse in the continuing flow of the carrier gas.

A glass tube 32 is retained in the housing 18 with an o-ring 34 near the top but below the inlet 22. The carrier gas (selectively containing a pulse of sample) flows through the tube down to the bottom of the injector. A fitting 42 holds the column at the bottom. The inlet point 43 for the column taps a small test portion of the continuing flow of carrier gas (selectively with the sample) to be passed into the column. Most or all of the balance of the carrier gas (with any sample therein) flows up through an annular passage 38 between the housing and the tube, and is passed out of an exit passage 44. It will be appreciated that details of the injector may differ from this example.

Unless turned off externally, a portion of the carrier gas is discharged through the passage 44. The carrier gas, for example, may be helium, nitrogen, hydrogen, air, or mixture such as argon and methane at a gage pressure of 0.007 to 10.5 kg/cm$^2$ (0.1–150 psig). As the system provides its own gas controls, the pressure from the carrier supply 45 (FIG. 1) into the system 10 need not be accurately maintained. Carrier flow rate, for example, may be 100 ml/min, with 1 ml/min being tapped to the column.

As indicated above, the mixing chamber 20 may be bounded on one side by a septum 26 for the sample input. In such a case, the chamber should have a nearby outlet passage 46 for a purge gas taken as a portion of the carrier gas passed along the septum. The purge gas, with a typical flow rate of about 2 ml/min, removes vapors emitted from the septum during operation at elevated temperature, vapors that otherwise could contaminate the carrier and its test sample flowing to the column. The purge gas passes through a fixed restrictor 47 (FIG. 1), such as a sintered, porous metal element, to an ambient space 48. (As used herein and in the claims, the term "ambient space" designates any region or condition at lower pressure than the system, and usually is the atmosphere, but may be a vacuum chamber, or a plenum to collect and filter the outflow, or any other subsequent arrangement to dispose, use or test the outflow.) An ordinary pressure regulator 49 (either mechanical or electrically controlled) maintains a constant pressure into the restrictor 47, so as to maintain the purge gas at a constant flow rate. A valve 51 is disposed in the purge line, but this is normally open for the operations of this invention. A flowmeter (not shown) may be disposed between the restrictor 47 and the ambient space.

The present system utilizes back-pressure column regulation preferably with electronic pneumatic control. In operation, carrier and sample injection to the column are achieved with regulation of both pressure and flow rate of the carrier. Preferably the operations are effected by a computer 56 including analog/digital converters 58 as required for input and output (with appropriate amplifier circuits), a processing unit 60 (CPU), memory 62 (RAM and disk), a keyboard 64 or other means for operator input, and a display by a monitor 66 and/or printer. The computer also processes and displays results from signals on an electrical line 68 from the column detector 16 which shows variations in its output depending on the injection of sample and its selective adsorption and desorption by, or partitioning into and out of, the active element in the column. It further is desirable to display operating pressures, and flows. Generally an appropriate computer with programming software and/or firmware is provided with a commercial chromatographic system, such as a Perkin-Elmer Model 1022 GC Plus integrator, which uses an Intel™ 80386 processor with "C" programming.

A gas inlet line 70 conveys the carrier gas at a controlled inlet flow rate from the gas source 45 to the inlet passage 22 into the injector 14. A flow control means 69 is a conventional or other desired type, and should include a pressure gage 71 at the control means inlet relative to atmosphere.

In the present embodiment, the flow means 69 includes a flow rate detector 74, a variable flow rate restrictor 72 and a feedback flow controller therebetween for closed loop operation. Advantageously, but optionally, a solenoid shutoff valve 73 is disposed in the inlet line 70. The flow rate detector 74 is located in the inlet line to detect the inlet flow rate. This detector advantageously comprises a fixed gas restrictor element 76 inserted in the inlet line 70, and a differential pressure detector 78 connected across the fixed restrictor, i.e. in parallel to each end 80, 82 of the restrictor element 76. With the restrictor element 76 being calibrated, a proportional signal from the differential detector provides a direct measure of the inlet flow rate. The restrictor may be a capillary tube, but preferably is a laminar flow type advantageously formed of a 0.64 by 0.64 cm plug of sintered porous type 316 stainless steel that provides a flow, for example, of 100 ml/min helium at 6.3 kg/cm$^2$ (90 psi) input with 0.7 kg/cm$^2$ (10 psi) drop across the restrictor. Other useful rates are from 1 to 300 ml/min. Calibration is effected readily by separately connecting the restrictor into a system with a measured flow rate.

A feedback flow controller is operatively disposed with the flow rate detector 74, particularly the pressure transducer 78, to regulate the variable restrictor 72 with respect to inlet flow rate so as to maintain the inlet flow rate constant. A suitable type restrictor is a variable orifice effected by an electromagnet moving a rod end over a small hole, such as a Porter Instrument Co. model EPC1001. An alternative is a needle valve on a threaded stem controlled by a stepper motor.

In one embodiment (not shown) the controller may be an electronic amplifier that modifies an electrical signal from the detector 74 to send a corresponding current to the variable restrictor 72 to adjust the restrictor appropriately. In an advantageous embodiment (as illustrated) the controller is incorporated into a portion of the computer program 90 that is utilized to operate the chromatographic system 10 and compute and display results. Such program may be in software or firmware.

The pressure signal from the transducer 78 is passed on one of a plurality of operative signal lines 92 connected between the computer 60 and the various detectors and control elements. This pressure signal is compared to the pressure set point, and the resulting difference is the error signal which is passed through a standard PID (proportional, integral derivative) control algorithm to compute the necessary restriction control signal. This computes the control signal which is directed through a digital/analog converter (or other signal converter as required) and amplifier to the restrictor control. Preferably, the flow rate that is maintained is a mass flow rate. In such case the computer program includes a modification that calculates the feedback signal to the restrictor from stored information on the gas characteristics, particularly viscosity, carrier supply pressure and gas temperature.

Figure 2:
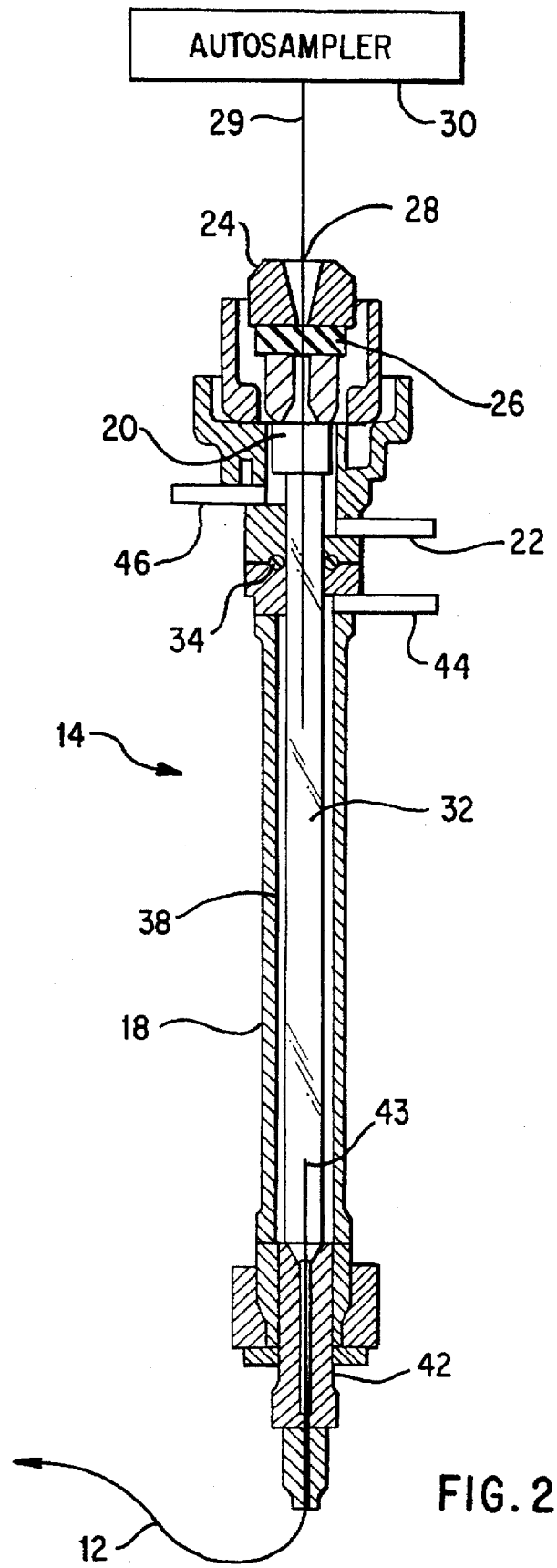
FIG. 2 is a longitudinal section of a conventional injector utilized in the system of FIG. 1.

In order to maintain a consistent flow rate through the chromatographic column, a substantially constant pressure should be maintained in the mixing chamber 20 (FIG. 2). To achieve this, the system further preferably has a primary pressure means 94 for regulating carrier gas flow through the outlet passage so as to maintain a constant, selected primary pressure into the column passage. This effects a back-pressure regulated mode.

The primary pressure means 94, which is a conventional or other desired back-pressure control, is connected in the split flow outlet between the exit passage 44 and the ambient space 48. This may be any type of pressure regulator such as mechanical. Preferably it utilizes a variable flow restrictor 96 which is a conventional or other desired gas valve device that can be regulated. This variable restrictor advantageously is the same type as for the flow control restrictor 72.

Advantageously a solenoid shutoff valve 98 is installed in the restrictor line 100 before (as shown) or after the restrictor 96. A carbon filter 88 should be installed in the outlet line before the restrictor to remove components from the sample that would clog the restrictor. A pressure transducer 102 is connected to measure pressure (relative to ambient) at the exit passage. A feedback controller from the transducer to the restrictor 96 is utilized, for example being the same type as for the flow controller, preferably through the computer. Another transducer 104 monitors ambient pressure relative to vacuum 105, which the computer incorporates into the pressure setpoints.

A sample transfer means, for example utilizing a sample receptacle 108, has access to a sample vessel 106, e.g. a vial which may be one of a plurality of vials in an autosampler which is conventionally automated such as in the Perkin-Elmer AutoSystem GC. The receptacle taps a portion of analyte sample from the vial. The sampling receptacle may be any conventional or other desired type that will serve the present purpose. A suitable receptacle (FIGS. 3a–3d) is a conventional Perkin-Elmer HS-40 Automated Headspace Sampler which is a modification of that described in U.S. Pat. No. 4,484,483, incorporated herein by reference.

In the receptacle 108 (see, for example, FIG. 3a), a needle 110 is disposed slidingly in a receptacle housing 112 through three o-rings 114, 116, 118 spaced apart so that an upper chamber 120 and a lower chamber 122 are delineated between the needle and the housing. The needle has a longitudinal hollow section 124 that terminates at its upper end with an upper transverse orifice 126, and at its lower end with a lower transverse orifice 128, each orifice communicating with the hollow section. The orifices are separated by about the same distance as the separation between adjacent o-rings. The needle has its upper end 130 affixed to a vertically movable sampling block (not shown) that moves the needle up and down through the o-rings, such that the orifices selectively communicate to the chambers or externally from the housing. Line 117 from a transfer pressure control source 119 and line 29 to the injector 14 (FIG. 1) and the column 12 are connected by a common gas line 132 to the lower chamber 122. The upper chamber 120 exits through a constrictor 144 that may be a needle valve for adjustment (but ordinarily is left unchanged), with shutoff valve 146. The transfer line has an inherent resistance 147 (FIG. 1) which allows pressure difference between the injector, as established by the primary pressure controller, and the receptacle 108. This resistance, if measured, may be used to compute flow rate in line 29 from the pressure difference. The transfer line may be, for example, 75 cm long by 0.25 mm inside diameter, effecting a 5 psi pressure drop.

The needle 110 can be lowered though the injector housing to the sample vial 106 that has a self-sealing diaphragm 148, e.g. a 0.5 cm thick disk of silicone rubber or the like. The needle pierces the diaphragm so that the lower orifice 128 penetrates into the vial to access the sample 134. The hollow section 124 of the needle thus may be in communication with the headspace of the sample vial.

The auxiliary or transfer pressure control means 119 (FIG. 1) applies selected pressure to the receptacle 108. Input to this auxiliary pressure source is from the main carrier gas supply 45. Although the transfer pressure 119 means may utilize any pressure regulator such as a mechanical type, this pressure means is conveniently the same type as preferred (and described above) for the primary back-pressure control 94. Thus, in a preferable embodiment, a variable constrictor 150 and a shutoff valve 152 are in series in the line 154 from the supply. A pressure transducer 156 measures pressure (relative to ambient) on line 117 into the receptacle and, by feedback control, varies the constrictor to maintain constant pressure. A dedicated amplifier or, preferably, the computer program is used to effect the feedback as described above for the back-pressure. A pressure regulator 158 with constrictor 160 to atmosphere is disposed between the variable constrictor and atmosphere, to function as a bleeder and an aid in the control of pressure in the auxiliary controller.

The system operates by cycling through four successive states, namely standby, pressurizing, transfer and venting. This may be achieved by manual control according to a method of the invention, but preferably is effected by the computer programming.

In the standby state (FIG. 3a), the needle 110 is raised so that the lower orifice 128 is in the lower chamber 122 of the housing 112 and the upper orifice 126 is in the upper chamber 120, so as to connect the two chambers by the hollow section of the needle. Carrier gas is supplied from the mass flow controller 69 through its open valve 73 to the injector 14, while the primary back-pressure regulator 94 controls the pressure in the injector according to the its pressure setpoint. The auxiliary valve 152 from the transfer gas pressure source 119 is open. The transfer gas pressure setpoint is set greater than the primary backpressure setpoint, e.g. 1.1 kg/cm$^2$ (15 psi) and 0.7 kg/cm$^2$ respectively, to provide flushing of old sample away from the injector inlet by the transfer gas. Alternatively the transfer pressure may be set less than the back-pressure setpoint so that, due to the reverse pressure, carrier gas flows backwards through the transfer line 29 from the injector inlet 22 to the receptacle system and exits through the bleed constrictor 144. If a constrictor valve 146 is used, it is open for this standby state, but may be closed thereafter for the remaining states.

In the next state, which is a pressurizing state (FIG. 3b), the carrier flow and primary back-pressure are continued. The auxiliary valve 152 remains open for the carrier flow. The transfer pressure controller 119 is set to the desired sample vessel pressurization setpoint which is a selected starting pressure greater than the primary back-pressure setpoint, e.g. 1.8 and 1.4 kg/cm$^2$ (25 and 20 psi) respectively. The receptacle needle 110 with its lower orifice 128 is inserted into the selected vessel 106, such that the upper orifice 126 communicates the vessel to the lower receptacle chamber 122. Gas flows from the transfer gas pressure regulator 119 into the sample vessel and the transfer line 29, pressurizing the gaseous sample up to a selected starting pressure in the vessel. The excess flow from the transfer line into the injector 14 is released through the back-pressure regulator 94 so that the lower back-pressure in the injector chamber remains constant.

Figure 3B:
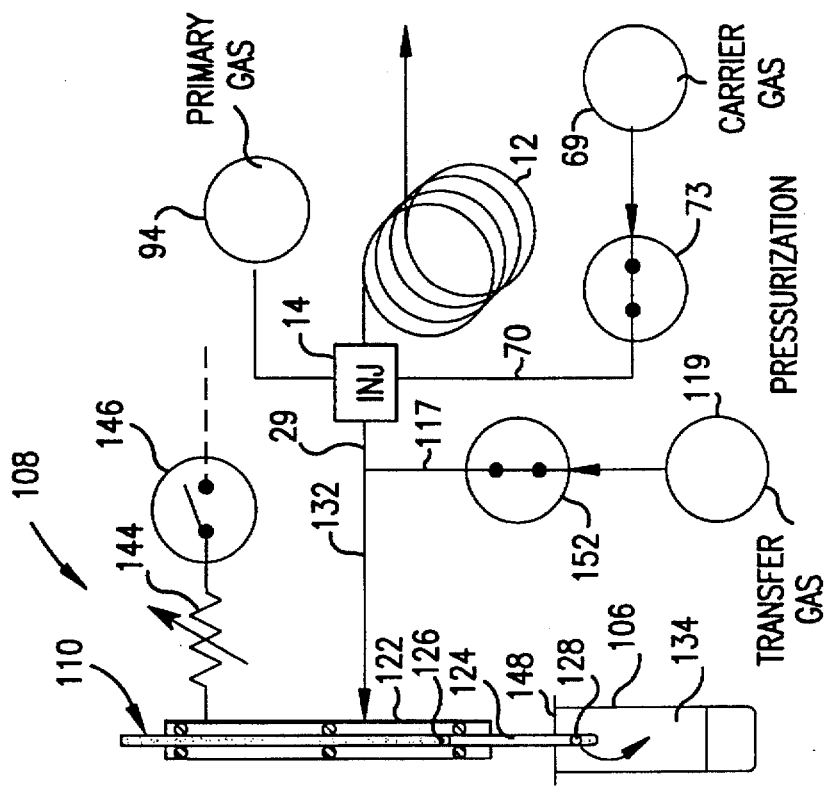
FIGS. 3a, 3b, 3c and 3d are schematic illustrations of four successive states of operation of the system of FIG. 1, and show schematic vertical sections of a receptacle component.
Figure 3A:
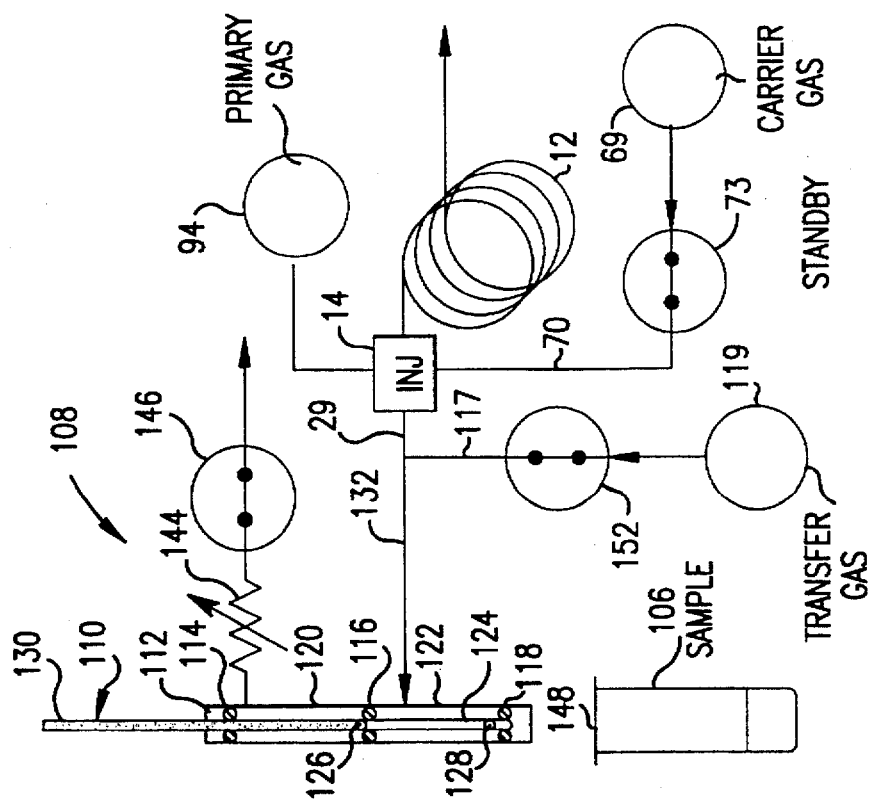
Figure 3D:
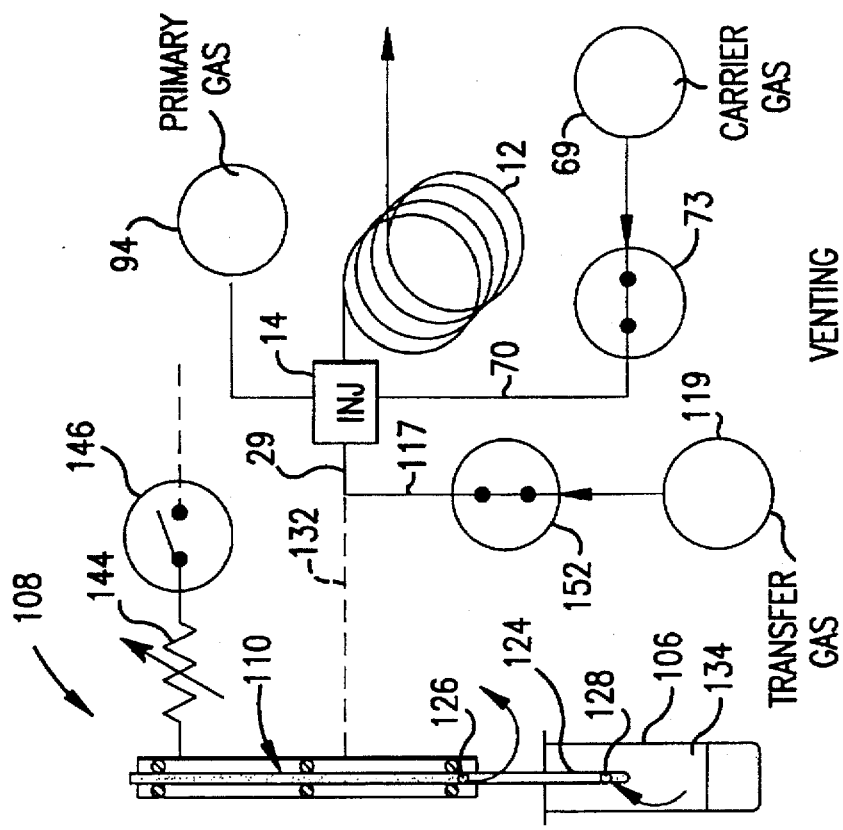
Figure 3C:
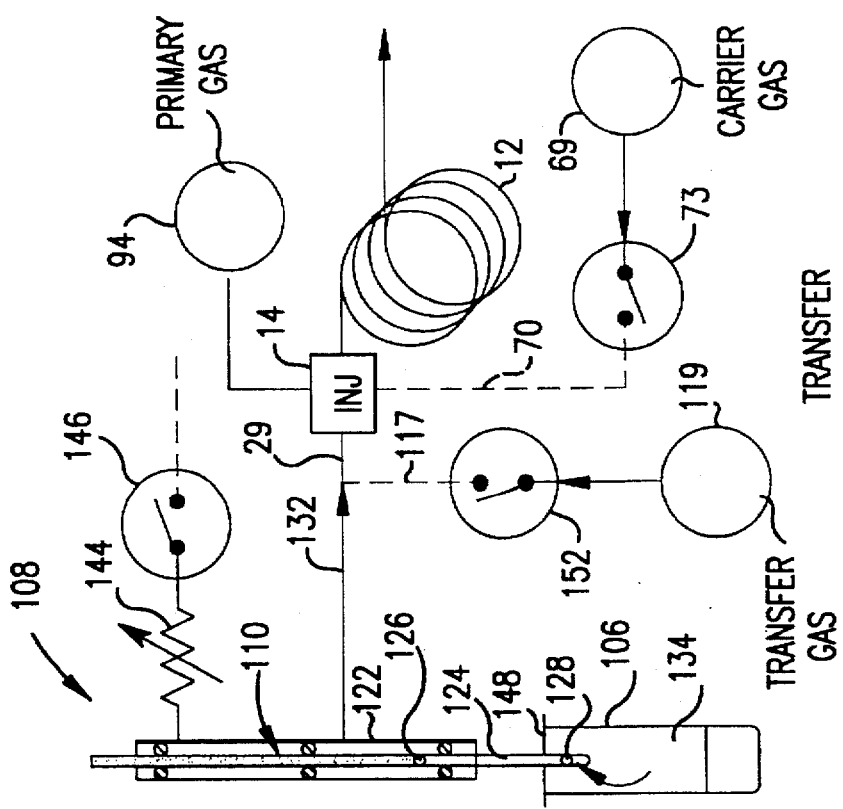

In the transfer state (FIG. 3c), carrier flow from its controller 69 is turned off with its associated valve 73 closed. The auxiliary valve 152 is closed, and the needle remains in the vessel 106. (In FIGS. 3b–3d, broken lines including lines 70 and 117 in FIG. 3b depict no flow in the relevant lines for the corresponding states.) Sample in the transfer gas flows from the vessel 106 through the hollow section 124 and the lower chamber 122 into the transfer line 29 as long as the sample vessel pressure remains greater than the primary back-pressure setpoint. Sample flow proceeds into the injector 14. During this time, because of the constant pressure in the injector, by release of excess gas through the regulator 94, flow of sample from the injector into the column remains constant even though the flow rate through the transfer line is decreasing, as flow out of the primary controller 94 decreases to compensate.

The carrier gas flow controller 69 and its valve 73 are continued off during sample transfer. The sample divides into the column and out the back-pressure regulator. As the flow of sample from the transfer line 29 decreases (due to the decreasing pressure in the vessel), the back-pressure regulator control resistance becomes more restrictive so as to maintain a constant pressure in the inlet. Under these conditions the column flow remains constant, and the total amount of sample transferred into the column is a linear function of the sampling time. Once the flow of sample from the transfer line decreases to approach the column flow rate, the back-pressure control valve becomes fully shut. The additional amount of sample transferred into the column would become nonlinear with the additional sampling time after this point is reached. Thus it is desirable to limit the sample transfer time period to less than this point.

If the mass flow controller 69 and its valve 73 were to be set on during sample transfer, the sample in the injector 44 would be diluted with additional carrier gas before entering the column. Since the sample flow rate from the transfer line is decreasing with time, the sample concentration in the now diluted carrier stream inside the inlet will decrease accordingly, and the sample amount transferred into the column will no longer be a linear function of sampling time. Therefore, carrier flow is set off for this state.

In the venting state (FIG. 3d), the needle 110 is lowered further into the vessel 106 to communicate the upper orifice 126 to atmosphere. In one alternative for this state, the system valves and setpoints may be set to the same conditions as for the standby state. Sample vents from the vessel 106 to atmosphere. Carrier flows from the injector 14 into the transfer line 29, effectively backflushing any remaining sample away from this line.

Preferably, for repetitive sampling from the same vessel (MHE technique, not shown in FIG. 3d), in the venting state the auxiliary valve 152 is left open, and the auxiliary pressure regulator absolute setpoint is adjusted to a level nominally greater than the ambient pressure, for example up to 6.3 kg/cm$^2$ (90 psi), such as 1.8 kg/cm$^2$ (25 psi) greater. Remaining sample in the vessel will vent out the restrictor 144 until the vessel pressure is equal to the transfer pressure controller setpoint. This action will ensure a consistent sample vessel pressure after venting, for subsequent sampling.

The system is returned to the standby state upon withdrawal of the needle from the sample vessel. This series of four states thus provides for introduction of sample into the column at a linear rate with time, the volume of sample being reproducible from one sampling to the next.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. A method for transferring analyte sample in a gas chromatographic system that includes a gas chromatographic column with a column inlet, injector means with a chamber selectively receptive of a carrier gas flow and an analyte sample in a transfer gas with the chamber communicating with the column inlet for injecting carrier gas and sample into the column, flow means for effecting a carrier gas flow into the chamber at a constant flow rate, primary pressure means for maintaining a constant primary pressure at the column inlet, a transfer pressure source of a transfer gas, and transfer means for selectively communicating a sample vessel with the transfer pressure source or the chamber, the sample vessel containing an analyte sample, wherein the method comprises steps of initially pressurizing the sample vessel with the transfer gas from the transfer pressure source so as to effect a vessel pressure at a starting pressure greater than the primary pressure, and communicating the sample vessel with the chamber so as to transfer analyte sample in the transfer gas from the sample vessel to the chamber by the vessel pressure while declining from the starting pressure during a transfer period, the transfer period being such that the vessel pressure while declining from the starting pressure remains greater than the primary pressure, with the pressurizing and the carrier gas flow discontinued, whereby analyte sample is transferred through the chamber into the column by the primary pressure linearly with time during the transfer period.

2. The method of claim 1 wherein the method further comprises venting the sample vessel to ambient atmosphere commencing upon termination of the transfer period, with communication between the sample vessel and the chamber discontinued, and carrier gas flow effected.

3. The system of claim 2 wherein the transfer means comprises a bleed line openable to atmosphere, and the method further comprises, with the bleed line open prior to pressurizing, flushing the transfer means with a flush gas selected from transfer gas or from carrier gas backflow from the chamber.

4. The system of claim 3 wherein the method further comprises selecting a transfer gas pressure greater than the primary pressure during the transfer period for the transfer gas to flush the transfer means.

5. The system of claim 3 wherein the method further comprises selecting a transfer gas pressure less than the primary pressure during the transfer period for the carrier gas backflow to flush the transfer means.

6. A gas chromatographic system comprising:

a gas chromatographic column with a column inlet;

injector means with a chamber selectively receptive of a carrier gas flow and an analyte sample in a transfer gas, the chamber communicating with the column inlet for injecting gas and sample into the column;

flow means for effecting the carrier gas flow into the chamber at a constant flow rate, including means for discontinuing the carrier gas flow during a transfer period;

primary pressure means for maintaining a constant primary pressure at the column inlet;

pressurizing means for pressurizing a sample vessel containing an analyte sample, the pressurizing being effected with the transfer gas to effect a vessel pressure at a starting pressure greater than the primary pressure; and transfer means for communicating the sample vessel with the chamber so as to transfer analyte sample in the transfer gas from the sample vessel to the chamber by the vessel pressure during the transfer period, the transfer period being such that the vessel pressure while declining from the starting pressure remains greater than the primary pressure, with the pressurizing and the carrier gas flow discontinued, whereby analyte sample is transferred through the chamber into the column by the primary pressure linearly with time during the transfer period.

7. The system of claim 6 wherein the transfer means includes means for venting the sample vessel to ambient atmosphere upon termination of the transfer period, with communication between the sample vessel and the chamber discontinued, and carrier gas flow effected.

8. The system of claim 7 wherein the pressurizing means comprises a transfer pressure source, the transfer means comprises a bleed line openable to atmosphere prior to the initial pressurizing and, with the bleed line open, the transfer means is receptive of a flush gas, selected transfer gas or carrier gas backflow from the chamber, so as to flush the transfer means.

9. The system of claim 8 further comprising means for selecting the transfer gas as the flush gas, wherein the transfer gas has a pressure greater than the primary pressure during the standby state for the transfer gas to flush the transfer means.

10. The system of claim 8 further comprising means for selecting the carrier gas from the chamber as the flush gas, wherein the transfer gas has a pressure less than the primary pressure during the standby state for the carrier gas backflow to flush the transfer means.

11. A gas chromatographic system comprising:

a gas chromatographic column with a column inlet;

injector means with a chamber selectively receptive of a carrier gas flow and an analyte sample in a transfer gas, the chamber communicating with the column inlet for injecting gas and sample into the column;

flow means for effecting the carrier gas flow into the chamber at a constant flow rate, including means for discontinuing the carrier gas flow during a transfer period; primary pressure means for maintaining a constant primary pressure at the column inlet;

a transfer pressure source of a transfer gas;

transfer means for selectively communicating a sample vessel with the transfer pressure source or the chamber, the sample vessel containing an analyte sample; and control means operatively connected with the transfer means for operating the chromatographic system through a set of operational states comprising, in sequence:

a pressurizing state for pressurizing the sample vessel with the transfer gas, with the sample vessel being in communication with the transfer pressure source so as to effect a vessel pressure at a starting pressure greater than the primary pressure; and a sample transfer state for transferring analyte sample in the transfer gas from the sample vessel to the chamber by the vessel pressure during a transfer period, the transfer period being such that the vessel pressure while declining from the starting pressure remains greater than the primary pressure, with the pressurizing and the carrier gas flow discontinued, whereby analyte sample is transferred through the chamber into the column by the primary pressure linearly with time during the transfer period.

12. The system of claim 11 wherein the transfer means includes means for selectively communicating the sample vessel to ambient atmosphere, and the set of operational states further comprises a venting state for venting the sample vessel to ambient atmosphere, the venting state commencing upon termination of the transfer period, with the sample vessel being in communication to ambient atmosphere, communication between the sample vessel and the chamber discontinued, and carrier gas flow effected.

13. The system of claim 12 wherein the transfer means comprises a bleed line openable to atmosphere, the transfer means is selectively receptive of a flush gas selected from transfer gas or from carrier gas backflow from the chamber, and the set of operational states further comprises a standby state prior to the pressurizing state, with the bleed line open and the transfer means receptive of the flush gas for the transfer means to be flushed by carrier gas or transfer gas during the standby state.

14. The system of claim 13 further comprising a transfer gas source of the transfer gas operatively connected with the control means, wherein the transfer pressure is selected by the control means so as to be greater than the primary pressure during the standby state for the transfer gas to flush the transfer means.

15. The system of claim 13 further comprising a transfer gas source of the transfer gas operatively connected with the control means, wherein the transfer pressure is selected by the control means so as to be less than the primary pressure during the standby state for the carrier gas backflow to flush the transfer means.

16. The system of claim 12 wherein the control means repetitively cycles the chromatographic system through the set of operational states with the same or a different sample vessel for each cycle.

* * * * *